United States Patent
Eason et al.

(10) Patent No.: US 8,739,784 B2
(45) Date of Patent: Jun. 3, 2014

(54) INHALER

(75) Inventors: Stephen William Eason, Cambridge (GB); Matthew Neil Sarkar, Cambridge (GB); Graham Roger Gibbins, Cambridge (GB); Ralf Thoemmes, Ingelheim am Rhein (DE); Jessica Frentzel-Beyme, Ingelhelm am Rhein (DE); Jens Besseler, Ingelheim am Rhein (DE); Timo Von Brunn, Ingelheim am Rhein (DE)

(73) Assignee: Vectura Delivery Devices Limited, Chippenham (GB)

( * ) Notice: Subject to any disclaimer, the term of this patent is extended or adjusted under 35 U.S.C. 154(b) by 754 days.

(21) Appl. No.: 12/864,181

(22) PCT Filed: Jan. 19, 2009

(86) PCT No.: PCT/EP2009/000294
§ 371 (c)(1),
(2), (4) Date: Feb. 7, 2011

(87) PCT Pub. No.: WO2009/092551
PCT Pub. Date: Jul. 30, 2009

(65) Prior Publication Data
US 2011/0114088 A1    May 19, 2011

(30) Foreign Application Priority Data

Jan. 24, 2008  (EP) ..................................... 08001307

(51) Int. Cl.
*A61M 15/00* (2006.01)
(52) U.S. Cl.
CPC ... *A61M 15/0045* (2013.01); *A61M 2015/0051* (2013.01); *A61M 2202/064* (2013.01)
USPC ............. 128/203.21; 128/203.12; 128/200.24

(58) Field of Classification Search
CPC ................... A61M 2202/064; A61M 15/0045; A61M 2015/0051; A61M 15/0028; A61M 2015/0055; A61M 15/0091; A61M 15/0065; A61M 2015/0036; A61M 2015/0041; A61M 15/0086; A61M 2015/0035; A61M 15/00; A61M 2015/0078; A61M 2015/0038; A61M 2015/004
USPC ............. 128/200.11–200.24, 203.12, 203.15, 128/203.19, 203.21
See application file for complete search history.

(56) References Cited

U.S. PATENT DOCUMENTS

| 5,415,162 A * | 5/1995 | Casper et al. ............ 128/203.12 |
| 8,408,201 B2 * | 4/2013 | Pocock et al. ........... 128/203.21 |

(Continued)

FOREIGN PATENT DOCUMENTS

| JP | 2005515039 A | 5/2005 |
| JP | 2007533363 A | 11/2007 |

(Continued)

OTHER PUBLICATIONS

Office action, dated Mar. 19, 2013, issued by the Japanese Patent Office in corresponding Japanese Application No. 2010-543422.

(Continued)

*Primary Examiner* — Annette Dixon
(74) *Attorney, Agent, or Firm* — Davidson, Davidson & Kappel, LLC

(57) ABSTRACT

An inhaler for delivery of a powder-form inhalation formulation from a blister strip with a plurality of blister pockets is proposed. A flexible guiding element receives the used blisters strip.

8 Claims, 4 Drawing Sheets

(56) References Cited

U.S. PATENT DOCUMENTS

Figure 1:
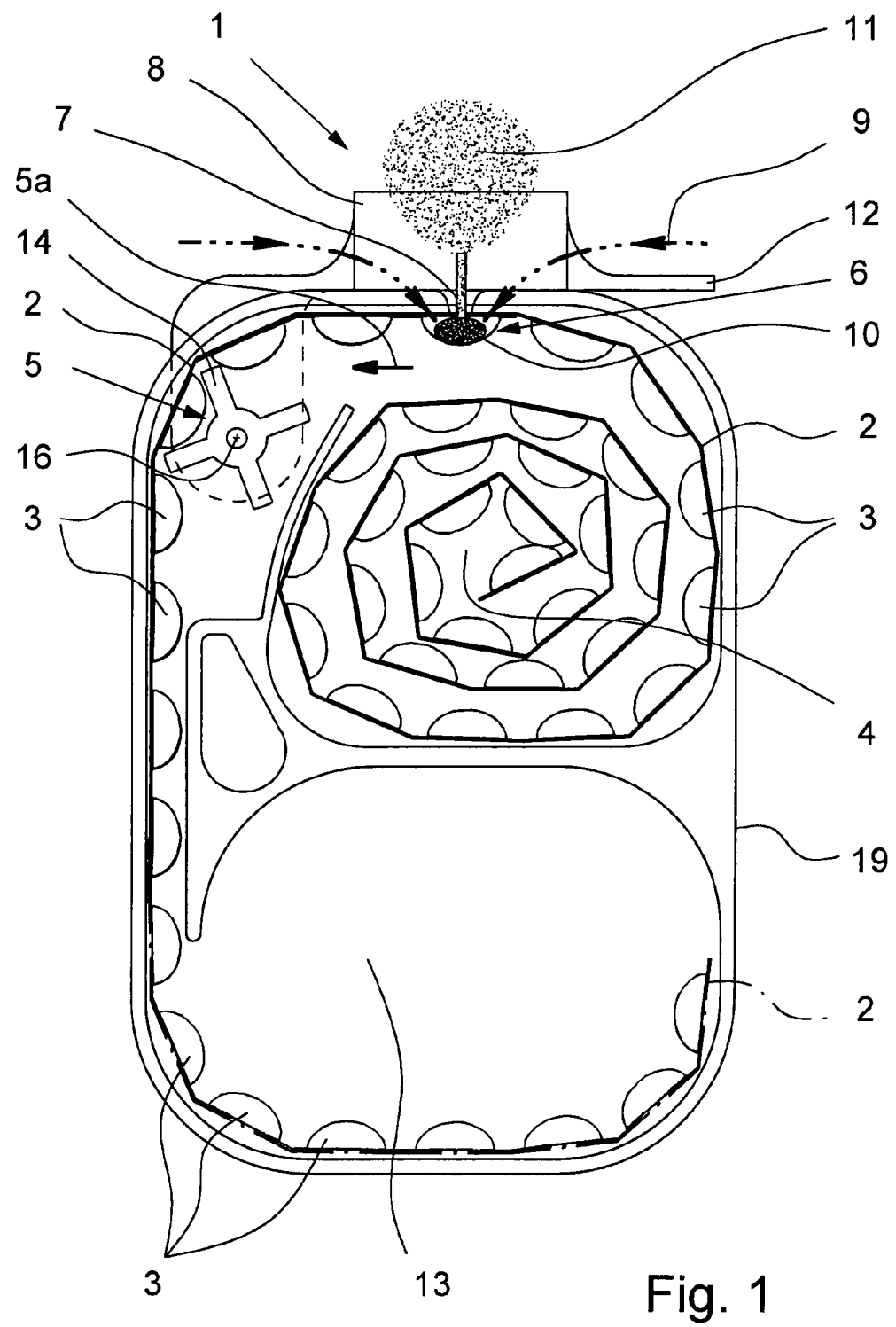

| | | |
|---|---|---|
| 2005/0126568 A1 | 6/2005 | Davies et al. |
| 2005/0154491 A1 | 7/2005 | Anderson et al. |
| 2006/0163269 A1 | 7/2006 | Anderson et al. |
| 2008/0099015 A1 | 5/2008 | Pocock et al. |
| 2009/0007908 A1* | 1/2009 | Eason et al. ............ 128/203.15 |
| 2010/0139654 A1 | 6/2010 | Thoemmes et al. |
| 2011/0132358 A1 | 6/2011 | Eason et al. |

FOREIGN PATENT DOCUMENTS

| | | |
|---|---|---|
| WO | 03/035508 | 5/2003 |
| WO | WO 2006079746 A | 8/2006 |
| WO | 2007/012871 | 2/2007 |
| WO | WO 2007096111 | 8/2007 |
| WO | 2007/118648 | 10/2007 |

OTHER PUBLICATIONS

International Search Report issued in connection with International Patent Application No. PCT/EP2009/000294.

Written Opinion of the international Searching Authority issued in connection with International Patent Application No. PCT/EP2009/000294.

* cited by examiner

INHALER

This application is a national phase application under 35 U.S.C. §371 of International Application No. PCT/EP2009/000294, filed Jan. 19, 2009, which claims priority to European Patent Application No. 08001307.1, filed Jan. 24, 2008, the disclosures of which are all hereby incorporated by reference herein.

FIELD OF THE INVENTION

The present invention relates to an inhaler (1) for delivery of an inhalation formulation from a preferably band-shaped blister strip with a plurality of blister pockets containing the inhalation formulation in doses comprising preferably a piercing member (7) to puncture a lid of an aligned blister pocket (3), the inhaler (1) being designed such that—preferably by breathing in during inhalation—an air stream (9) of ambient air can be sucked or delivered in to discharge the respective dose from an opened blister pocket (3) and to deliver it with the ambient air as an aerosol cloud (11), characterized in that the inhaler (1) comprises a flexible or elastic guiding element (20) for receiving or guiding the blister strip (2), wherein the guiding element (20) comprises a mounting portion (21) with a corrugation (22), the guiding element (20) is held between a first and a second holding portion (23, 24), in particular with the mounting portion (21), the guiding element (20) or mounting portion (21) is at least partially covered by a guiding portion (28), and/or the guiding element (20) comprises a free end (25) or a slit (27) with two tip and/or two tapered portions (26) so that the guiding element comprises (20) a free end (25) with the highest curvature, flexibility or elasticity of the guiding element (20). The present invention also relates to an inhaler (1) for delivery of an inhalation formulation from a preferably band-shaped blister strip (2) with a plurality of blister pockets (3) containing the inhalation formulation in doses, preferably according one of the preceding claims, comprising: preferably a piercing member (7) to puncture a lid of an aligned blister pocket (3), the inhaler (1) being designed such that—preferably by breathing in during inhalation—an air stream (9) of ambient air can be sucked or delivered in order to discharge the respective dose from an opened blister pocket (3) and to deliver it with the ambient air as an aerosol cloud (11), characterized in that the inhaler (1) comprises a metal guiding element (20) for receiving or guiding the blister strip (2), the guiding element (20) being electropolished in order to reduce the sliding resistance of the blister strip (2) on the guiding element (20).

The present invention relates to an inhaler for delivery of a powder-form inhalation formulation from a blister strip with a plurality of blister pockets (also called blisters) containing the inhalation formulation in doses.

BACKGROUND

GB 2 407 042 A discloses an inhaler with a rolled-up blister strip. The inhaler comprises a manually operated, pivotable actuator which operates a conveyor for stepwise moving the blister strip. The actuator supports a piercer and an associated mouthpiece. By pivoting the actuator, the blister strip and be moved forward and blister pockets of the blister strip can be pierced one after the other. When a patient breathes in an air stream passes through the pierced blister pocket, with the result that the inhalation formulation in the blister pocket mixes with the air and is discharged to the patient.

SUMMARY OF THE INVENTION

Object of the present invention is to provide an inhaler with simple and/or compact construction, which allows optimized conveying and/or storage of the blister strip.

The above object is achieved by an inhaler according to the present invention. Advantageous embodiments are discussed in detail below.

One aspect of the present invention is to provide a flexible or elastic guiding element, preferably in the shape of a spiral, wherein the guiding element comprises a mounting portion with a corrugation, is held between a first and a second holding portion, is at least partially covered by a guiding portion in the mounting portion, and/or comprises a free end and/or a slit with two tip portions, so that it comprises a free end with the highest curvature, flexibility and/or elasticity of the guiding element. This allows a simple and compact construction with optimized conveying and/or storage of the preferably used blister strip.

According to an or additional aspect of the present invention, the inhaler comprises a metal guiding element, which is electropolished in order to reduce the sliding friction of the blister strip on the guiding element. This allows also a simple and compact construction with optimized conveying and/or storage of the blister strip.

Further aspects, features, properties and advantages of the present invention are described in the claims and the subsequent description of a preferred embodiment, with reference to the drawing. There are shown in:

BRIEF DESCRIPTION OF THE DRAWINGS

FIG. 1 a schematic sectional view of an inhaler without mouthpiece cover;

FIG. 2 a schematic sectional representation of the inhaler with closed mouthpiece cover; and FIG. 3 a partial, enlarged view of FIG. 2; and FIG. 4 a perspective view of a guiding element of the inhaler.

In the Figures, the same reference numbers are used for identical or similar parts, even if a repeated description is omitted. In particular identical or corresponding advantages and properties then also result or may be achieved.

DETAILED DESCRIPTION

FIG. 1 shows in a schematic sectional representation an inhaler 1.

The inhaler 1 serves to deliver a powdered inhalation formulation from a band-shaped blister strip 2. The blister strip 2 is finite, not forming an endless or closed loop. It has a large number of blister pockets 3 respectively containing directly a dose of the loose inhalation formulation. Thus, the formulation is pre-metered.

The inhaler 1 has a reservoir 4 for the still unused blister strip 2 with closed (sealed) blister pockets 3. The blister strip 3 is rolled up or wound up in the reservoir 4. In the representation example the reservoir 4 is formed such that the blister strip 2 can be moved outwards or pulled out of the reservoir 4 as easily as possible.

In the representation example the blister strip 2 is directly received in the reservoir 4. However, instead of this a cassette, a container, a drum or suchlike can also be fitted or inserted with the blister strip 2 into the inhaler 1 or the reservoir 4.

The inhaler 1 has a conveyor 5 for stepwise onward movement in direction of arrow 5*a* by one blister pocket 3 in each case, in order to feed the blister pockets 3 successively to an opening and/or removal position 6 where the respective blister pocket 3 is opened and can be emptied.

The blister pockets 3 can be opened respectively preferably by means of a piercing member 7, which punctures cuts open a lid of the respectively aligned blister pocket 3 in position 6. The piercing member 7 is hollow and in fluid connection with an adjacent mouthpiece 8 of the inhaler 1.

During or for inhalation a patient or user, not represented, places the mouthpiece 8 in his mouth and breathes in. The respectively opened blister pocket 3, into which the piercing member 7 extends, is thereby emptied by sucking in. An air stream 9 of ambient air is sucked in and passed through the opened blister pocket 3 such that the loose powder 10 (forming the inhalation formulation and being schematically shown in FIG. 1 only in the actually opened blister pocket 3 below mouthpiece 8) is dispensed with the sucked-in ambient air as an aerosol cloud 11 via the mouthpiece 8. This situation is schematically represented in FIG. 1.

The inhaler 1 has a preferably manually actuatable, lever-like actuator 12 being pivotally mounted to a housing 19 of the inhaler 1.

The piercing member 7 and the mouthpiece 8 are attached to and supported by the actuator 12.

The actuator 12 is operable (pivotable) to cause the piercing member 7 to puncture the lid of the respectively aligned blister pocket 3 in position 6 below the mouthpiece 8.

When the actuator 12 swivels from the position shown in FIG. 1 (here anti-clockwise) to a opened position, the piercing member 7 is withdrawn from the last-pierced blister pocket 3.

Then, the blister strip 2 is moved forward one blister pocket 3, so that the next blister pocket 3 is moved in position 6.

When the actuator 12 swivels back into the position shown in FIG. 1, i.e. is manually moved back, the next aligned blister pocket 3 of the blister strip 2 is punctured by the piercing member 7 and thereby opened. Then, the next inhalation can take place, i.e. the inhaler 1 is activated.

The inhaler 1 has a receiving space or apparatus 13 to receive or store the used part of the blister strip 2. The receiving space or apparatus 13 is preferably formed such that the used part can be wound up. FIG. 1 shows a situation with essentially filled reservoir 4 and still essentially empty receiving space 13.

The conveyor 5 comprises a conveying wheel 14, which can engage between the blister pockets 3 and thus convey the blister strip 2 in form-locking or form-fit manner. This allows very secure or precise moving or indexing of the blister strip 2 as desired and/or necessary.

The conveyor 5 or its conveying wheel 14 is arranged between the reservoir 4 and the receiving apparatus 13, in particular between the removal position 6 and the receiving apparatus 13, thus after the emptying of the blister pockets 3.

The pivot axis 16 of the actuator 12 is coaxial with the rotation axis of the conveying wheel 14. In particular, the actuator 12 may be supported by an axle of the conveying wheel 14.

Figure 2:
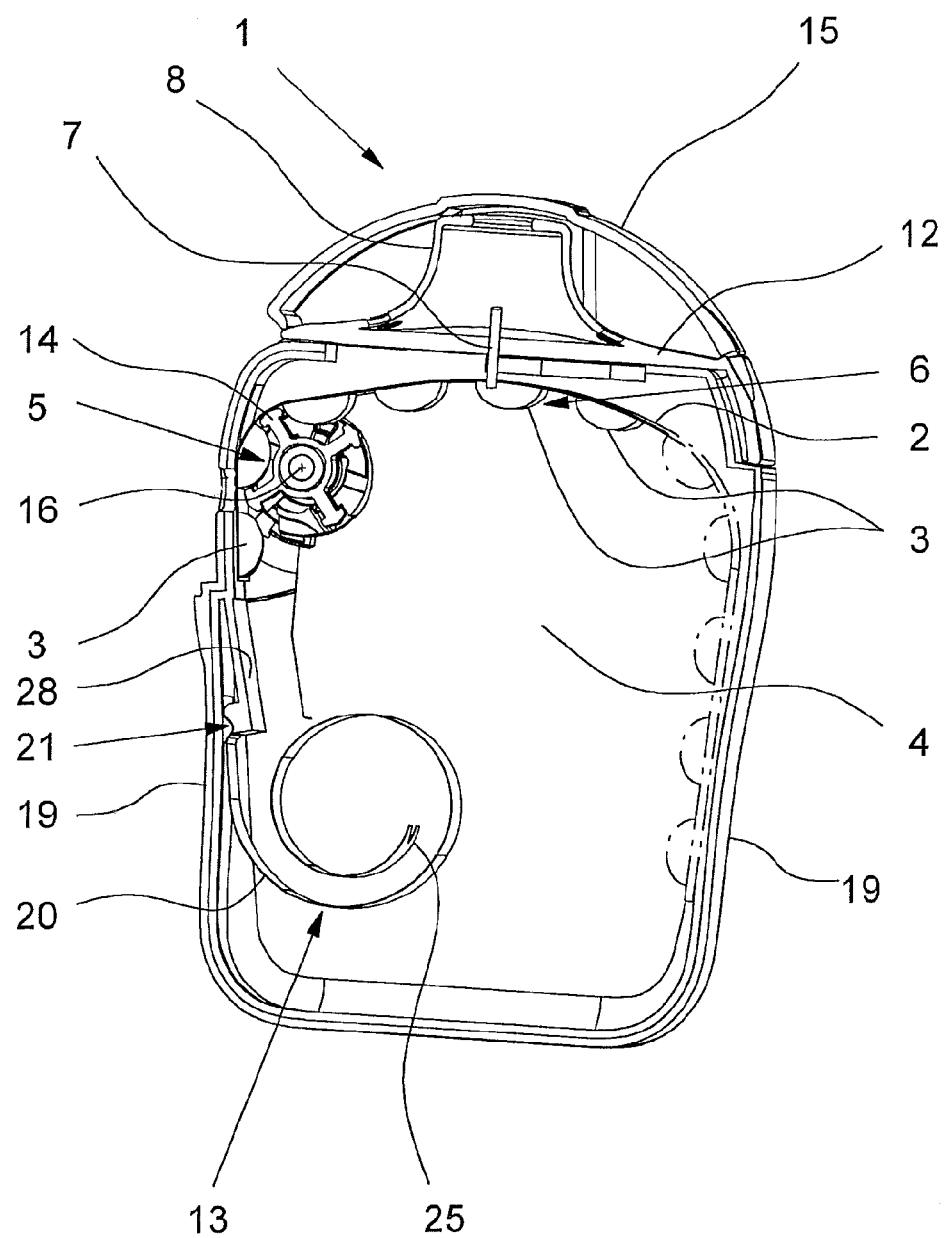

The inhaler 1 comprises a mouthpiece cover 15. The mouthpiece cover 15 is not shown in FIG. 1 which explains the basic principle of the inhaler 1, but in FIG. 2 which shows a more realistic, but still schematic sectional view of the inhaler 1. FIG. 2 shows the inhaler 1 with closed mouthpiece cover 15, wherein the blister strip 2 has been partly omitted for illustration purposes.

The inhaler 1 or its receiving apparatus 13 comprises a guiding element 20 for receiving and/or guiding the blister strip 2, in particular the used part of the blister strip 2.

The guiding element 20 is preferably flexible and/or elastic. It is preferably made of metal, in particular spring steal.

The guiding element 20 is preferably mounted or fixed at a mounting portion 21, in particular only at this portion 21.

Figure 3:
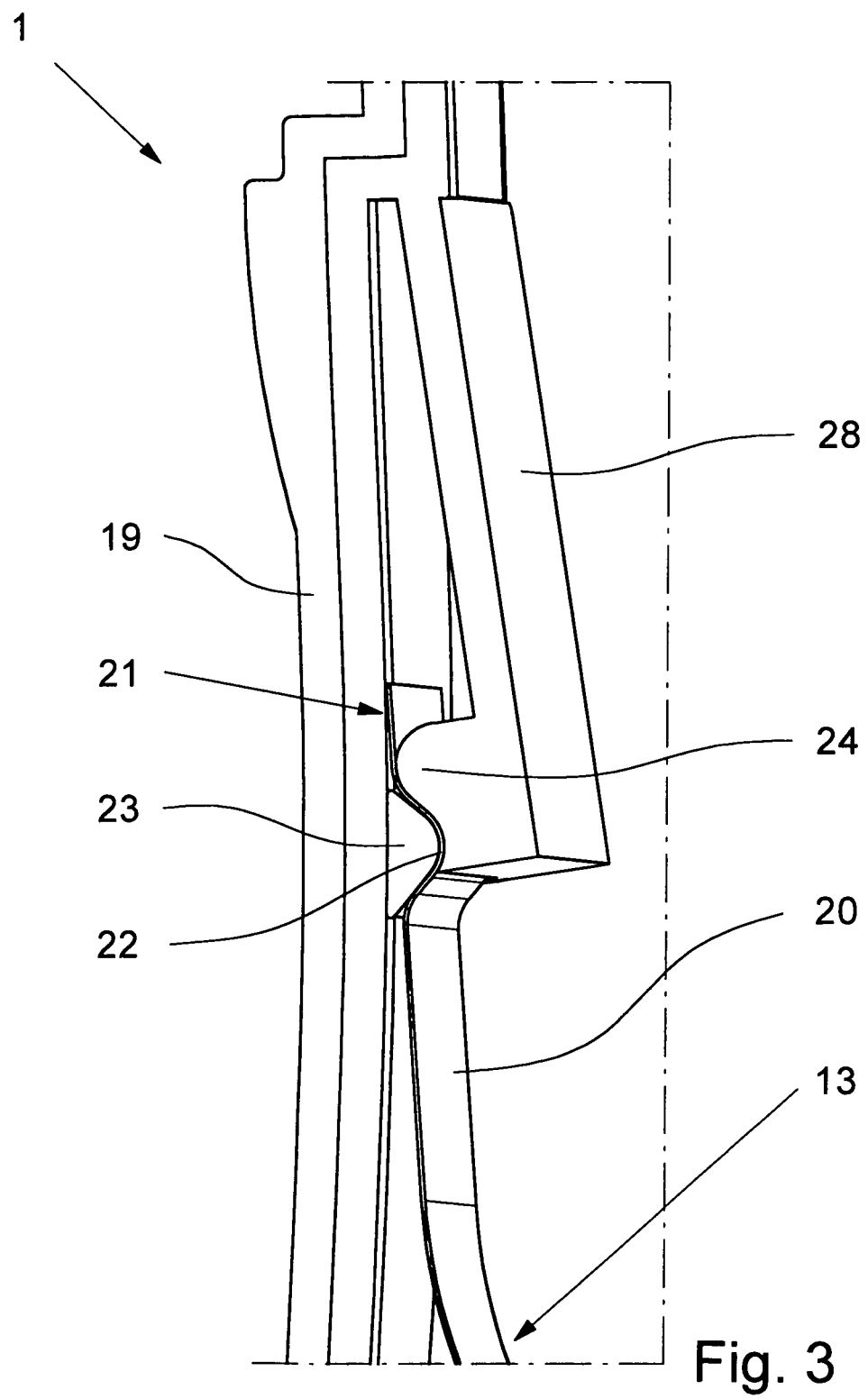
Figure 4:
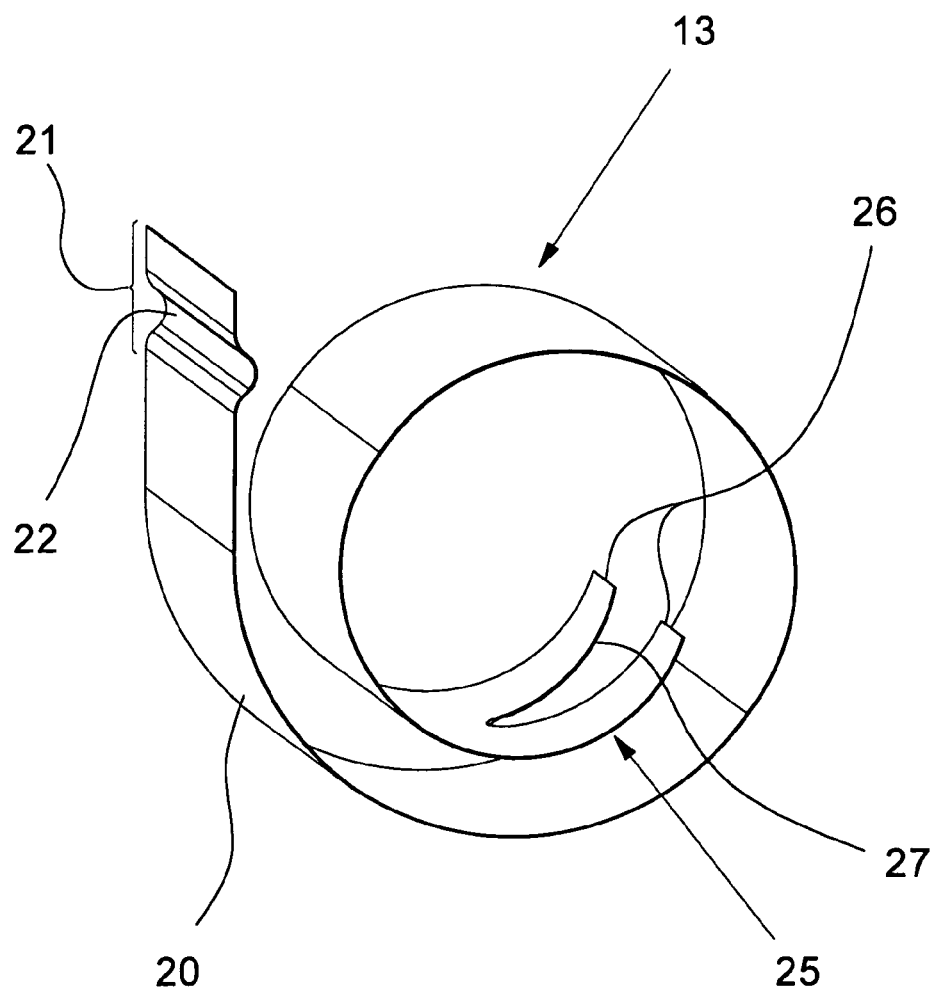

FIG. 2 shows the open inhaler 1 with the mounted guiding element 20. FIG. 3 shows in an enlarged, partial view of FIG. 2 the area of the mounting portion 21 of the guiding element 20. FIG. 4 shows the guiding element 20 alone, in particular in its pre-fabricated form or state.

Preferably the guiding element 20 comprises a spiral portion or has the form essentially of a spiral.

The guiding element 20 is preferably held by form-fit at a mounting end, in particular at its mounting portion 21. However, it can have any other suitable form.

Preferably, the mounting portion 21 is essentially straight, but bent or folded, and/or comprises a corrugation 22, as schematically shown in FIGS. 3 and 4. This facilitates the preferred form-fit mounting.

In the present embodiment, the mounting portion 21 with a corrugation 22 is held between a first holding portion 23 and a second holding portion 24 as shown in particular in FIG. 3. The holding portions 23, 24 are preferably stationary and/or molded and/or interconnected with or formed by housing 19 of the inhaler 1 or any other suitable component of the inhaler 1.

Preferably, the first holding portion 23 and the second holding portion 24 are formed by different halves of the housing 19 or by the same half of the housing 19.

In particular, the holding portions 23 and 24 comprise inbetween or form a slit for receiving or holding the guiding element 20 or its mounting portion 21. The opposing surfaces of the two holding portions 23, 24 are preferably essentially complementary.

Preferably, the guiding element 20 may be inserted into one half of the housing 19 in a first step. Then, the housing 19 is closed by the second half of the housing 19 in a second step so that the mounting portion 21 is held in a form-fit manner in the housing 19.

The guiding element 20 preferably comprises a free end 25 or a slit 27 with two tip and/or two tapered portions 26. This facilitates optimized guidance of the blister strip 2.

In the present embodiment, the free end 25 has essentially the form of the tongue of a snake, i.e. with two tip portions 26 with the longitudinally extending slit 27 and increasing distance in between towards the end.

In particular, the free end 25 comprises the highest curvature, flexibility and/or elasticity of the guiding element 20.

The slit 27 and/or tapered portion 26 (as outlined above) facilitates production of the guiding element 20 and, in particular, avoids that fins or ribs resulting from production can stop or hinder the blister strip 2, in particular its free end.

The inhaler 1 comprises preferably a guiding portion 28 as shown in FIGS. 2 and 3. The guiding portion 28 is preferably inclined and/or like a ramp. The guiding portion 28 facilitates entry or insertion of the free end or tip of blister strip 2 into the guiding element 20. Thus, it is facilitated to convey and in particular push the blister strip 2 into the guiding element 20 without any handicap.

The guiding portion 28 is preferably formed by the housing 19, in particular molded integrally with one half of the housing 19.

When the blister strip 2 is conveyed, it is preferably pushed into the guiding element 20. The blister strip 2 is wound up in the guiding element 20. The free end 25 causes the free end of the blister strip 2 to bend inwardly in particular such that a winding core is formed by the inwardly bent end of the blister strip 2.

With increasing conveying of the blister strip 2 into the guiding element 20, the guiding element 20 is expanded radially and/or guides the used blister strip 2 at its outer part, in particular the winding formed inside or in the center of the guiding element 20.

In order to reduce the sliding resistance of the blister strip 2 on the guiding element 20, the guiding element 20 is preferably polished, in particular electrically or electrophoretically polished.

Preferably, the guiding element 20 is made of a high quality steel, in particular of steel 1.4302. In particular, the guiding element 20 is made from a metal band with a thickness of about 0.08 to 0.10 mm, preferably of about 0.09 mm, a length of about 100 to 150 mm, and/or a width of about 16 to 18 mm.

The guiding element 20 described above allows an optimized guidance and/or storage of the blister strip 2, wherein a very simple and compact construction is possible. Further, simple mounting is possible.

Preferably, the inhaler 1 is portable, works only mechanically and/or is hand-held.

Preferably, the terms "blister strip" and "blister pockets" have to be understood in a very broad sense to cover also other kinds of storage means with receptacles or even bulk storages for the formulation.

LIST OF REFERENCE NUMBERS 1 inhaler
2 blister strip
3 blister pocket
4 reservoir
5 conveyor
5a onward movement
6 opening and/or removal position
7 piercing member
8 mouthpiece
9 air stream
10 powder
11 aerosol cloud
12 actuator
13 receiving apparatus
14 conveying wheel
15 mouthpiece cover
19 housing
20 guiding element
21 mounting portion
22 corrugation
23 first holding portion
24 second holding portion
25 free end
26 tip portion
27 slit
28 guiding portion

The invention claimed is:

1. Inhaler for delivery of an inhalation formulation from a band-shaped blister strip with a plurality of blister pockets containing the inhalation formulation in doses, comprising:
a piercing member to puncture a lid of an aligned blister pocket, the inhaler being designed such that—by breathing in during inhalation—an air stream of ambient air can be sucked or delivered in to discharge the respective dose from an opened blister pocket and to deliver it with the ambient air as an aerosol cloud,
wherein
the inhaler comprises a flexible or elastic guiding element for receiving or guiding a used portion of the blister strip, wherein
the guiding element comprises a mounting portion with a corrugation,
the mounting portion is held between a first and a second holding portion,
the guiding element or mounting portion is at least partially covered by a guiding portion.

2. Inhaler according to claim 1, wherein the guiding element is made of steel.

3. Inhaler according to claim 1, wherein the first and second holding portion are molded and are formed by a housing of the inhaler or by separate halves of the housing.

4. Inhaler according to claim 1, wherein the first and second holding portion are at least essentially complementary.

5. Inhaler according to claim 1, wherein the first and second holding portion form a slit in between for receiving the guiding element or the mounting portion.

6. Inhaler according to claim 1, wherein the first or second holding portion forms the guiding portion.

7. Inhaler according to claim 1, wherein the guiding portion is inclined or ramp-like to facilitate conveying the blister strip into the guiding element.

8. Inhaler according to claim 1, wherein the guiding element comprises a free end having a slit with two tip or two tapered portions so that the guiding element comprises the highest curvature, flexibility or elasticity at the free end of the guiding element.

* * * * *